(12) United States Patent
Stafford

(10) Patent No.: US 10,231,861 B1
(45) Date of Patent: Mar. 19, 2019

(54) PHYSICAL TRAINING DEVICE

(71) Applicant: Paul J. Stafford, Tucson, AZ (US)

(72) Inventor: Paul J. Stafford, Tucson, AZ (US)

( * ) Notice: Subject to any disclaimer, the term of this patent is extended or adjusted under 35 U.S.C. 154(b) by 447 days.

(21) Appl. No.: 15/056,594

(22) Filed: Feb. 29, 2016

Related U.S. Application Data

(60) Provisional application No. 62/128,360, filed on Mar. 4, 2015.

(51) Int. Cl.
*A61F 5/01* (2006.01)
*A61F 5/30* (2006.01)

(52) U.S. Cl.
CPC ............ *A61F 5/0118* (2013.01); *A61F 5/30* (2013.01)

(58) Field of Classification Search
CPC .......... A61F 5/0118; A61F 5/30; A61F 5/013; A61F 5/05858; A61F 5/3753; A61F 5/3738; A61F 5/05875; A61F 5/05866
USPC .......................................................... 602/20
See application file for complete search history.

(56) References Cited

U.S. PATENT DOCUMENTS

| 5,288,254 | A | 2/1994 | Elson .............................. 441/56 |
| 5,864,518 | A | 1/1999 | Geiser ............................. 368/10 |
| 6,144,620 | A | 11/2000 | dePoortere .................... 368/108 |
| 6,487,906 | B1 | 12/2002 | Hock ......................... 73/379.01 |
| 6,955,542 | B2 | 10/2005 | Roncalez et al. ............. 434/254 |
| 7,033,281 | B2 | 4/2006 | Carnahan et al. ............ 473/221 |
| 7,037,286 | B1 * | 5/2006 | Reinhardt ............. A61F 5/0118 |
| | | | 128/878 |
| 7,044,818 | B2 | 5/2006 | Askins ............................ 441/55 |
| 7,874,997 | B2 * | 1/2011 | Jaccard ................. A61F 5/0118 |
| | | | 128/846 |
| 7,887,497 | B2 * | 2/2011 | Weber ................... A61F 5/0118 |
| | | | 128/878 |
| 8,406,085 | B2 | 3/2013 | Sakita ............................. 368/10 |
| 2002/0082538 | A1 * | 6/2002 | Holland ................ A61F 5/0118 |
| | | | 602/21 |
| 2002/0198472 | A1 | 12/2002 | Kramer ........................ 600/595 |
| 2004/0106889 | A1 * | 6/2004 | Robinson .............. A61F 5/0118 |
| | | | 602/64 |
| 2004/0203301 | A1 | 10/2004 | Johnson .......................... 441/56 |
| 2008/0287848 | A1 * | 11/2008 | Jaccard ................. A61F 5/0118 |
| | | | 602/21 |
| 2010/0210975 | A1 | 8/2010 | Anthony, III et al. ........ 600/595 |
| 2010/0234182 | A1 * | 9/2010 | Hoffman ............. A61B 5/1125 |
| | | | 482/8 |
| 2011/0149694 | A1 | 6/2011 | Sakita ............................. 368/10 |
| 2011/0153042 | A1 | 6/2011 | Burton et al. .................. 700/91 |

(Continued)

*Primary Examiner* — Ophelia A Hawthorne
(74) *Attorney, Agent, or Firm* — Hayes Soloway P.C.

(57) ABSTRACT

A physical training device is provided herein. The device may include a brace portion and a fastening mechanism for securing the device to a user's limbs, digits, joints, shoulders, legs, knees, ankles, feet, back, neck, head and/or joints. The device may prevent or limit movement of a user's limbs, digits, joints, shoulders, legs, knees, ankles, feet, back, neck, head and or/joints. The device may also include a brace portion having a spiral or helical shape such that it may be wrapped around a user's limbs, digits, joints, shoulders, legs, knees, ankles, feet, back, neck, head and/or joints. The device may also include a sensor for detecting movement of a user's limbs, digits, joints, shoulders, legs, knees, ankles, feet, back, neck, head and/or joints, as well as a feedback device to notify the user when movement is detected.

15 Claims, 13 Drawing Sheets

(56) References Cited

U.S. PATENT DOCUMENTS

2014/0031703 A1 1/2014 Rayner et al. ................ 600/484
2014/0228649 A1 8/2014 Rayner et al. ................ 600/301

* cited by examiner

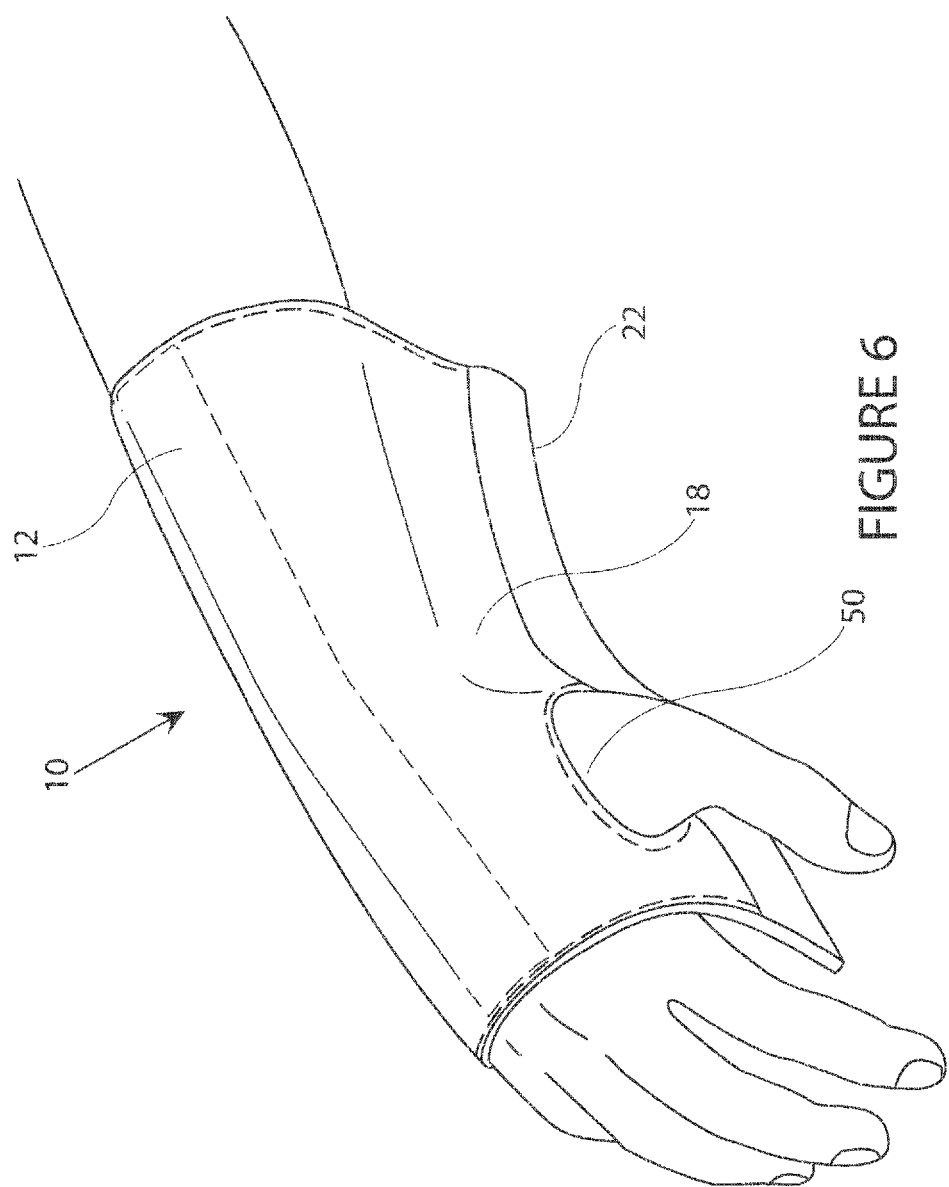

PHYSICAL TRAINING DEVICE

CROSS REFERENCE TO RELATED APPLICATION

This Application claims priority from U.S. Provisional Application Ser. No. 62/128,360, filed Mar. 4, 2015.

FIELD OF THE DISCLOSURE

This disclosure relates to a system that may be used for various forms of athletic or activity training, physical rehabilitation, or injury prevention. The disclosure has particular utility in connection with training of swimmers and will be described with such utility although other utilities are contemplated, including, without limitation various sports activities as will be described below, as well as physical rehabilitation and physical therapy. The system may limit or prevent movement of a user's joint or other body parts and may also provide tactile feedback to a user based on a variety of stimuli, including the position, movement, and/or rotation of a user's limbs, digits, joints, shoulders, back, head, neck or hips and/or other parts of the body.

BACKGROUND OF THE DISCLOSURE

Attaining proper physical form and technique is an important aspect of numerous types of athletic training, as well as injury prevention and physical rehabilitation. Learning to acquire proper form and technique is particularly important in the sport of swimming. To properly execute a swimming stroke, including the four primary strokes (i.e., freestyle, backstroke, breaststroke, butterfly), a swimmer must be aware of the position and movement of his or her various body parts throughout the entire stroke. Maintaining proper or preferred body position and movement allows the swimmer to execute the stroke in the most desirable manner (e.g., the most efficient and/or powerful stroke). Proper or preferred body position or movement may further serve to prevent injury to the swimmer. Moreover, while certain positions and movements of body parts during a particular swimming stroke may be generally recommended to all swimmers as the proper or preferred positions or movements, some swimmers may find that more individualized variations of preferred body position and movement during a stroke allow the swimmer to better achieve his or her desired results. Moreover, the proper or preferred positions and/or movements of these body parts may change for different swimming strokes, as well as during a single swimming stroke.

While a swimmer may be taught or shown proper or preferred body position and/or movements for executing a swimming stroke, maintaining such proper or preferred positioning and/or movement while actually practicing the stroke in water may often be difficult. A swimmer's body position and/or movement may deviate from the proper or preferred position and/or movement without the swimmer being aware. In fact, the swimmer may believe that he or she is practicing a stroke with the proper or preferred body position and/or movement when in fact he or she is not.

Among the body part positions with which a swimmer is concerned while executing a swimming stroke is maintaining proper positions of the arms, wrists, hands and fingers, including all corresponding joints. The positions and orientations of these body parts may affect both the swimmer's propulsions through the water, as well as the drag the swimmer experiences. In most cases, the swimmer looks to maximize propulsion while minimizing drag. Accordingly, the swimmer must be aware of factors such as the location, angles, rotation and the extension of these body parts, among other factors, throughout the stroke, including at the time of entry into, movement through, and exit from the water. These factors further should be considered not just for each individual body part alone, but also in relation to the other parts of the body.

Maintaining or learning to maintain proper or preferred positioning of body parts, and particularly the arms, wrists, hands, fingers, shoulders, legs including knees, ankles and feet, hack, head, neck or hips is also important in several other sports and athletic activities, including, for example, golf, tennis, racquetball, baseball, softball, volleyball, yoga, boxing, and other track and field sports and activities. Other persons who may find maintaining proper positioning of the arms, wrists, hands, fingers, shoulders, legs including knees, ankles and feed, back, head, neck or hips to be important include persons engaged in physical therapy or physical rehabilitation, as well as persons who wish to achieve a proper or preferred position of the arms, wrists, hands, fingers, shoulders, legs including knees, ankles and feet, back, head, neck or hips while completing other activities (e.g., typing) in order to avoid injury or improve technique. Often times, such movements may be repetitive, while other times the participant may simply desire to maintain a particular position for a particular length of time. However, participants in these various sports and activities may also find it difficult to maintain such proper or preferred positions while actually engaged in practicing or performing the sport or activity.

Accordingly, there exists a need heretofore unmet in the relevant field to address the needs of participants in the sports and activities described above with respect to training and learning to repetitively perform actions with a proper or preferred positioning and movement of body parts, including the arm, wrist, hand, fingers, shoulders, legs including knees, ankles and feet, back, head, neck or hips.

SUMMARY OF THE DISCLOSURE

Embodiments of the present disclosure provide a physical training device. Briefly described, one embodiment of a physical training device, among others, can be implemented as follows. The device may comprise a brace portion and a fastening mechanism for securing the brace portion adjacent to or in contact with a user's arm, wrist, hand, fingers, shoulders, legs including knees, ankles and feet, back, head, neck or hips. The brace portion may prevent or limit movement of a user's arm, wrist, hand, fingers, shoulders, legs including knees, ankles and feet, back, head, neck or hips when secured adjacent to or in contact with a user's arm, wrist, hand, fingers, shoulders, legs including knees, ankles and feet, back, head, neck or hips.

In another embodiment, the present disclosure provides a physical training device including a brace portion having a spiral or helical shape such that the brace portion includes one or more loops. The one or more loops of the brace portion may wrap around a user's arm, wrist, hand, fingers, shoulders, legs including knees, ankles and feet, back, head, neck or hips such that the brace portion may prevent or limit movement of a user's arm, wrist, hand, fingers, shoulders, legs including knees, ankles and feet, back, head, neck or hips when wrapped around a user's arm, wrist, hand and/or fingers.

In another embodiment, the present disclosure provides a physical training device including a sensor and a fastening mechanism. The sensor may detect movement of a user's arm, wrist, hand, fingers, shoulders, legs including knees, ankles and feet, back, head, neck or hips. The device may optionally provide feedback to the user when movement is detected.

The features, functions, and advantages that have been discussed can be achieved independently in various embodiments of the present disclosure or may be combined in yet other embodiments, further details of which can be seen with reference to the following description and drawings.

Other features, functions and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims.

BRIEF DESCRIPTION OF THE DRAWINGS

Many aspects of the disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIG. 6 shows a sixth exemplary embodiment of a physical training device in accordance with the present disclosure.

DETAILED DESCRIPTION

Figure 1:
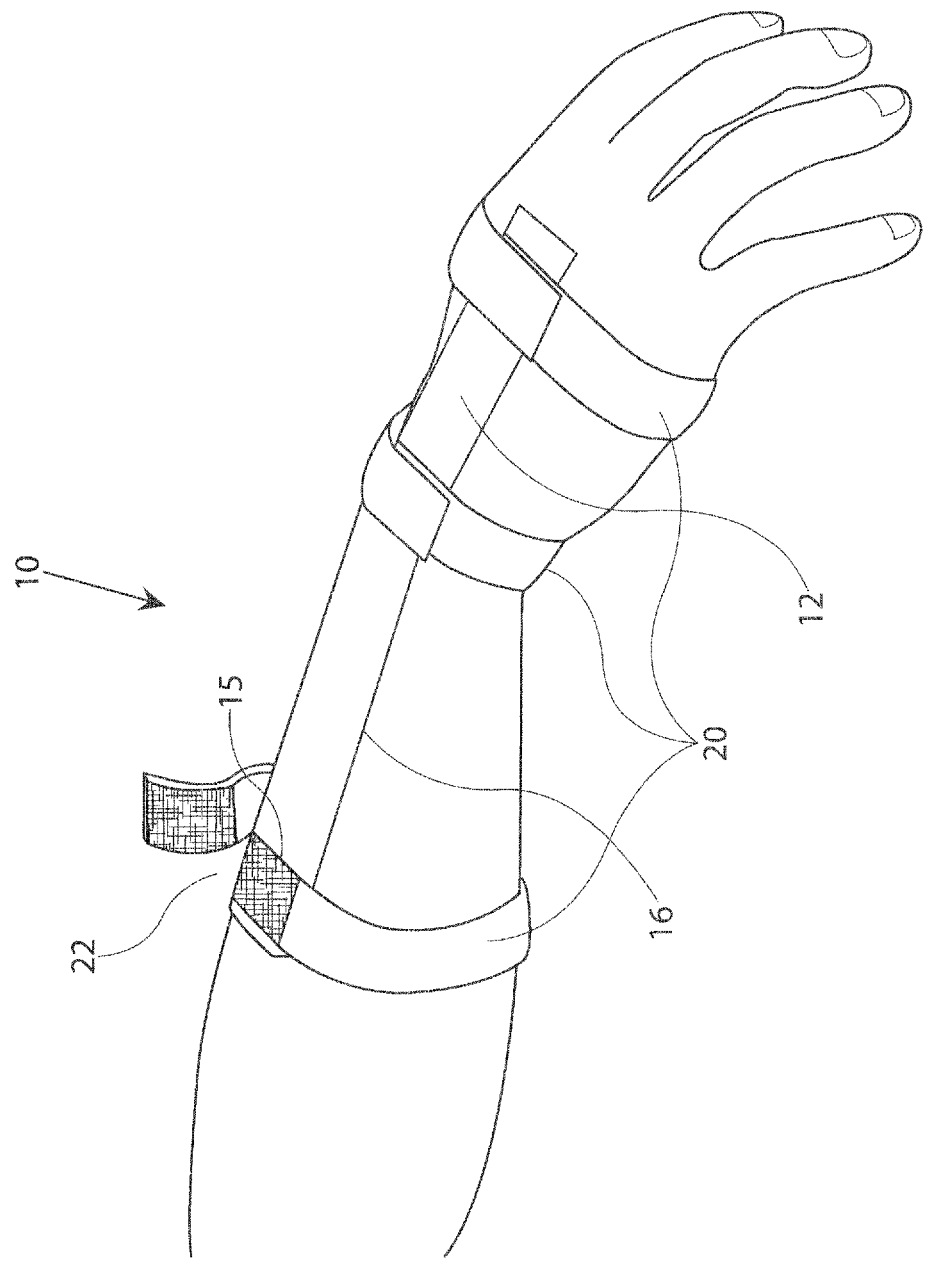
FIG. 1 shows a first exemplary embodiment of a physical training device in accordance with the present disclosure.

FIG. 1 shows a physical training device according to a first exemplary embodiment of the present disclosure. The physical training device 10 includes a brace portion 12. The brace portion 12 will be positioned adjacent to and/or in contact with the user's arm, wrist, hand and/or fingers when in use. The brace portion 12 should be stiff or rigid or semi-rigid such that it prevents or limits certain movements of the user's arm, wrist, hand and/or fingers when in use. Some degree of flexibility in the brace portion may be desirable, for example, to provide a more comfortable fit or experience for a user while still preventing or limiting certain movements. The brace portion may prevent or limit all movement of a particular body part or only a certain movement or movements of the body part. The brace portion 12 thereby serves to help the user maintain a particular or preferred position of the arm, wrist, hand and/or fingers when in use. The brace portion 12 may be flat, curved, partially curved, bent or partially bent, and the degree and/or amount of such flatness, curvature or bending may be adjustable to accommodate different users or to accommodate different positions of the arm, wrist, hand and/or fingers for a single user.

The brace portion 12 may comprise a number of different materials and configurations. Preferable materials include those that are hard, strong, film and/or lightweight. The materials may also be water-proof or resistant and/or sweat-proof or resistant to accommodate use of the device in a variety of activities and environments. Metals known in the art such as aluminum, titanium, steel and alloys thereof may be used to form the brace portion or part of the brace portion. The metal may be plated, e.g., with chrome. Similarly, rubbers, silicone rubbers, molded rubbers, polymers and plastics known in the art may also be used. The brace portion 12 may further comprise various combinations of any two or more of the materials noted above or other materials known in the art. In a preferred embodiment, the brace portion 12 comprises aluminum.

The size and length of the brace portion 12 may vary in different embodiments. In one embodiment, the brace portion may extend from the user's hand, across the wrist, to approximately mid-way up the forearm. However, the brace portion 12 may alternatively be extended in either direction, e.g., up toward the user's elbow, over the user's fingers, or both. The brace portion may similarly be shortened such that it only covers a single body part such as, for example, covering a user's wrist or only extending a short distance beyond a user's wrist in one or both directions (i.e., toward the user's hand and/or toward the user's arm). The width and depth of the brace portion 12 may also be uniform along its entire length or may vary along the length of the brace portion.

The brace portion 12 may comprise a single part or multiple parts. As is shown in FIG. 1, in a preferred embodiment the brace portion 12 comprises a single flat strip of material. Alternatively, the shape of the brace portion may be varied to include other similar known shapes in the art including, e.g., rods, slats. Also, the brace portion 12 may comprise two or more parts of the same or different shapes. Furthermore, when multiple parts are used, they may be in contact with or separated from one another. Brace portion 12 may further comprise padding 16.

Referring again to FIG. 1, the physical training device 10 further comprises a fastening mechanism 14 for securing the device adjacent to and/or in contact with a user's arm, wrist, hand and/or fingers. Securing the device in this manner allows the user to selectively use the device to preclude or limit movement of a particular body part. In one embodiment, the fastening mechanism 14 may comprise one or more straps 20 that may fully or partially wrap around a user's arm, wrist, hand and/or fingers. In an exemplary embodiment, the fastening mechanism comprises three straps. The straps may comprise a soft and/or flexible material that is comfortable when worn against a user's skin, including many cloths, fabrics and similar materials known in the art. The material will also preferably be water-proof or resistant and/or sweat-proof or resistant. In a preferred embodiment, the material may comprise sewn nylon. Alternatively, a nylon mesh, silicone rubber or molded rubber material may be used. Furthermore, as an alternative to or in addition to one or more straps, the fastening mechanism may comprise other fasteners including a sleeve, partial sleeve, cuff and/or glove.

The one or more straps 20 are attached to the brace portion 14. In a preferred embodiment, an adhesive 15 may be used. Alternatively, the one or more straps 20 may be attached to the brace portion 14 via sewing of the strap to or around the brace portion or fainting the strap from the same material as the brace portion.

As is shown in FIG. 1, the fastening mechanism may comprise hook and loop fasteners such as Velcro fasteners 22 for securing or fastening the device to a user's arm, wrist, hand and/or fingers. Both sides of the Velcro fasteners may be attached to the one or more straps 20, as is shown in FIG. 1. Alternatively, one side of the Velcro fasteners may be attached to the brace portion 14. Multiple pieces of Velcro fasteners or Velcro fasteners of varying sizes and lengths may provide an adjustable closure mechanism and thus may be used to provide a more or less secure fit according to the individual user and his or her own characteristics and preferences. Alternatively, the fastening mechanism may be secured via other closure mechanisms, including a keyhole closure, snap, button, zipper, hook and eyelet closure, magnet, elasticized straps or bands, or combinations of any of the foregoing. Further, the fastening mechanism may be secured via any of these mechanisms at any part of the device, including top, bottom, sides, etc.

Figure 2A:
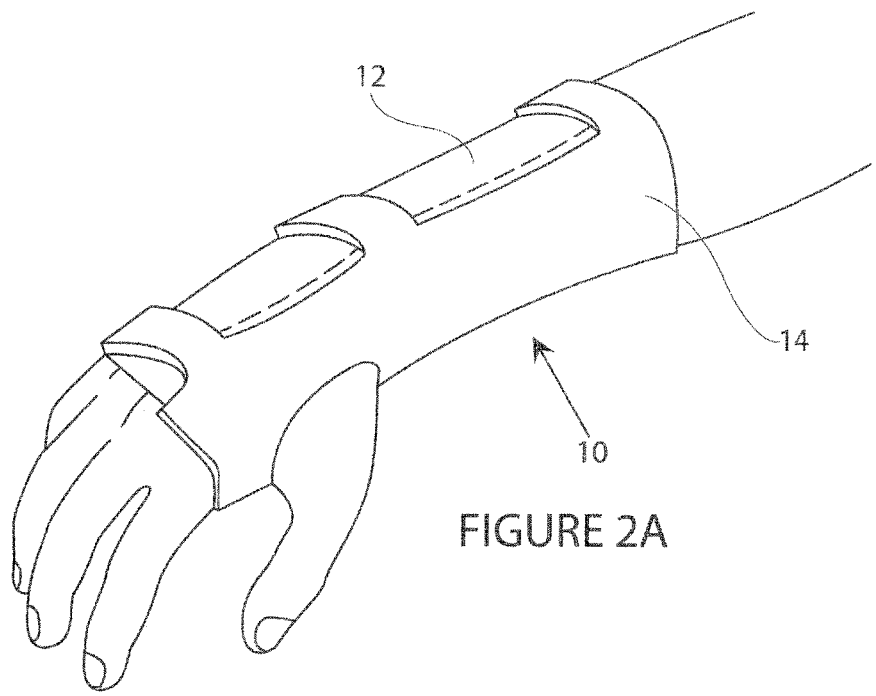
FIGS. 2a and 2b show a second exemplary embodiment of a physical training device in accordance with the present disclosure.
Figure 2B:
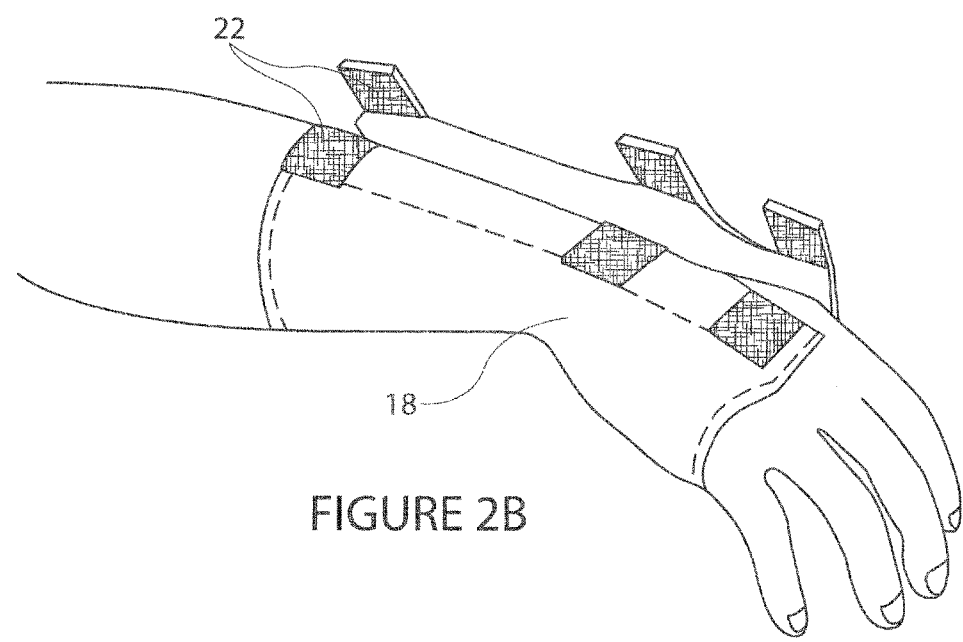

Referring now to FIGS. 2A and 2B, a second exemplary embodiment of a physical training device 10 is shown. According to this embodiment, fastening mechanism 14 may comprise sleeve 18 that may be worn over a user's arm, wrist, hand and/or fingers. The sleeve 18 may fully or partially cover a user's arm, hand, wrist and/or fingers, and alternatively may be configured as a partial sleeve, cuff, or glove. To accommodate a user's fingers, including in certain embodiments the user's thumb, one or more cutouts or holes may be formed into sleeve 18. The sleeve may comprise any suitable material, including nylon, nylon mesh, silicone rubber, molded rubber, vinyl, polymers, fabric, cloth and other similar materials. Preferably, the sleeve comprises sewn nylon fabric. Brace portion 12 may be sewn into the fabric of the sleeve, as is shown in FIG. 2A, or alternatively, may be attached to the sleeve via, for example, an adhesive. Sleeve 18 of fastening mechanism 14 may be configured as a sheet or strip of material that is put on by a user by wrapping around a user's arm, wrist, hand and/or fingers. Accordingly, the sleeve may further comprise one or more Velcro fasteners 22 for securing sleeve 18 around or on a user's arm, wrist, hand, and/or fingers. Alternative closures, as described above, may be used in place of or in addition to the Velcro fasteners. Alternatively, the sleeve may be tubular in design such that a user may pull it on over the fingers, hand, wrist and/or arm. The sleeve may be designed to fit snugly or tightly, but comfortably, against a user's body and may conform or partially conform to the shape of the user's arm, wrist, hands and/or fingers.

Figure 3:
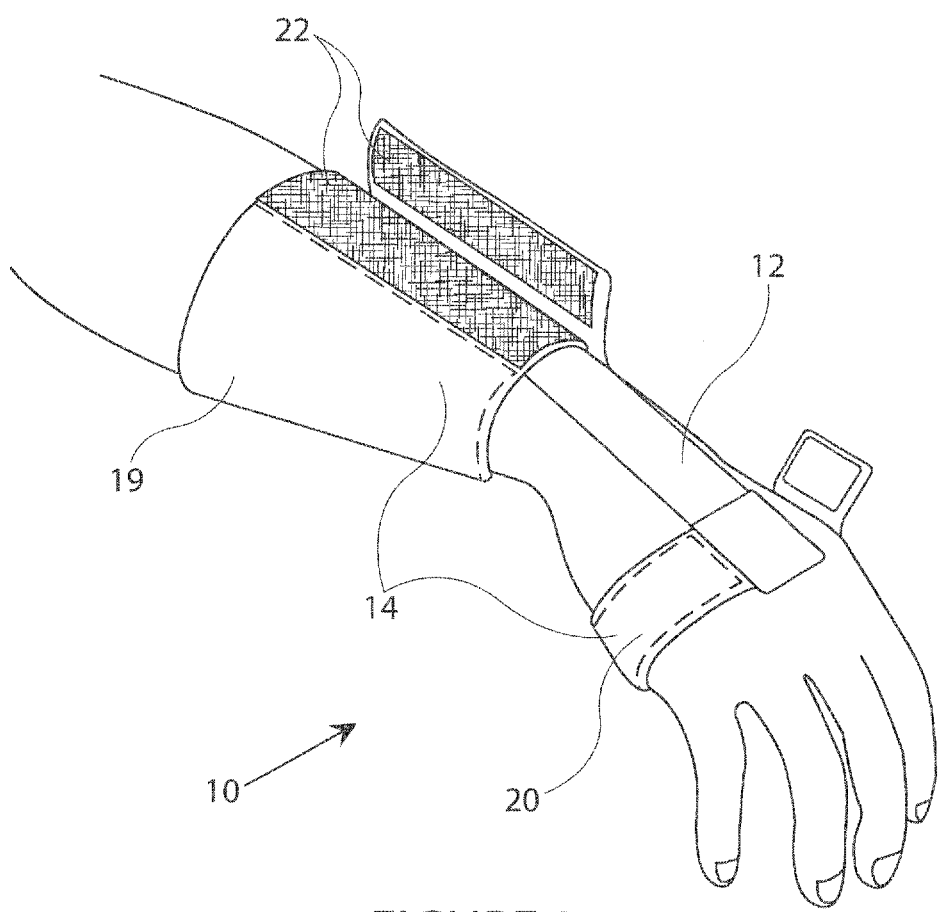
FIG. 3 shows a third exemplary embodiment of a physical training device in accordance with the present disclosure.

FIG. 3 shows a third exemplary embodiment of a physical training device 10. According to this embodiment, fastening mechanism 14 comprises a combination of a cuff 19 and a strap 20. As is shown in FIG. 3, the cuff 19 may wrap around or otherwise fit over a user's arm, while the strap 20 may wrap around or otherwise fit over a user's hand. Fastening mechanisms 14 comprising other combinations of a cuff and one or more straps are also possible, as are combinations including any of a sleeve, cuff, glove, and one or more straps. The positioning on a user's arm, wrist, hand and/or fingers of a sleeve, cuff, glove, and one or more straps may also vary. Brace portion 12 may be as described above and may be sewn into or otherwise adhered or attached to cuff 19 and/or strap 20, as shown in FIG. 3. Cuff 19 and strap 20 may each individually comprise any of the materials described above with respect to other embodiments. In a preferred embodiment, both cuff 19 and strap 20 comprise sewn nylon. Velcro fasteners 22 in various shapes and sizes may be used to secure cuff 19 and strap 20. As described above, other closure mechanisms may also be used to secure cuff 19 and strap 20.

Figure 4A:
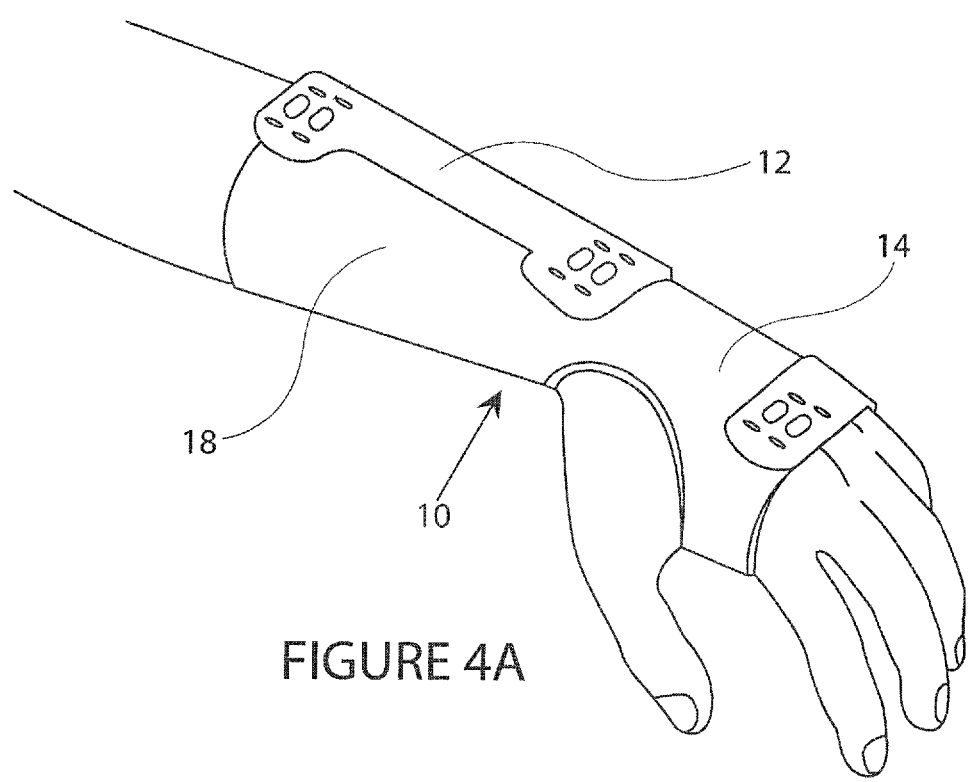
FIGS. 4a and 4b show a fourth exemplary embodiment of a physical training device in accordance with the present disclosure.
Figure 4B:
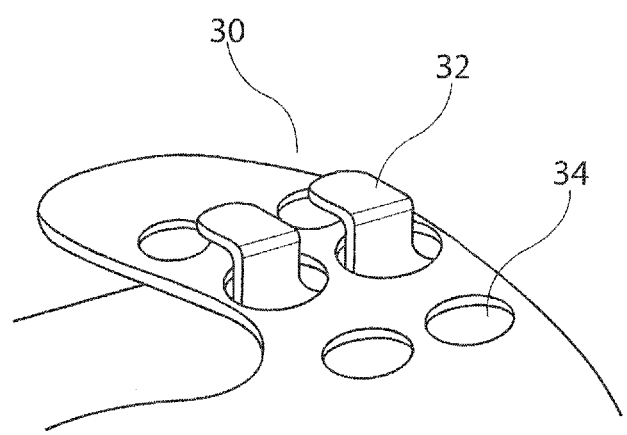

FIGS. 4a and 4b show a fourth exemplary embodiment of a physical training device 10 according to the present disclosure. In this embodiment, physical training device 10 comprises a brace portion 12 as described above with respect to previous embodiments. Preferably, brace portion 12 comprises aluminum and is bonded or otherwise attached to a fastening mechanism 14, which comprises a vinyl sheet. The vinyl sheet forms a sleeve 18, as described above. As shown in FIG. 4B, sleeve 18 may be secured to a user's arm, wrist, hand and/or fingers via one or more hook and eyelet closures 30. Closure 30 comprises at least one hook 32 and at least one eyelet 34 such that the hook may be securely inserted into the eyelet. Preferably, the hook and eyelet closure 30 comprises pairs of hooks 32 and pairs of eyelets 34. Multiple hooks 32 and/or eyelets 34 may be used to provide the user with an adjustable and customizable fit. The hooks 32 may be offset and/or bent or curved in order to provide a more secure closure and to prevent the closure 30 from coming apart accidently or unintentionally. This embodiment may further include variations to the brace portion 12 or fastening mechanism 14 as are described above with respect to other embodiments.

Figure 5A:
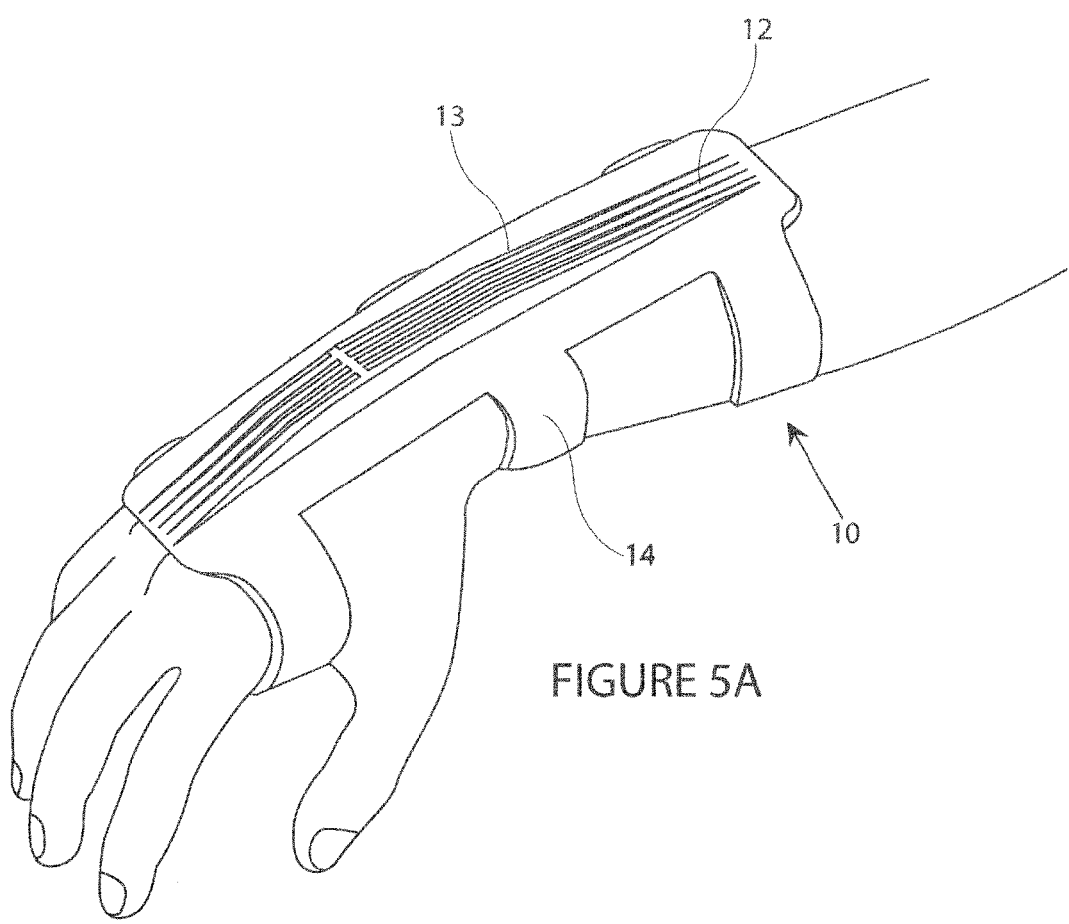
FIGS. 5a-5c show a fifth exemplary embodiment of a physical training device in accordance with the present disclosure.
Figure 5B:
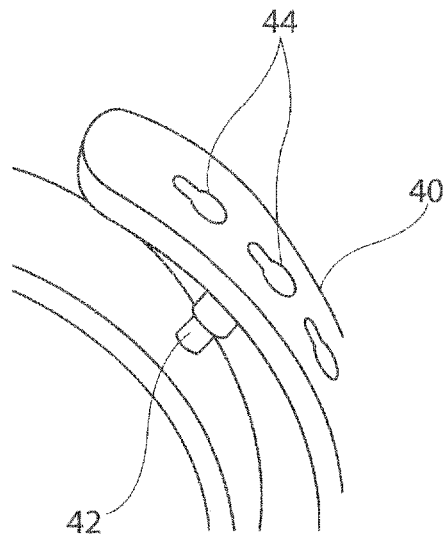
Figure 5C:
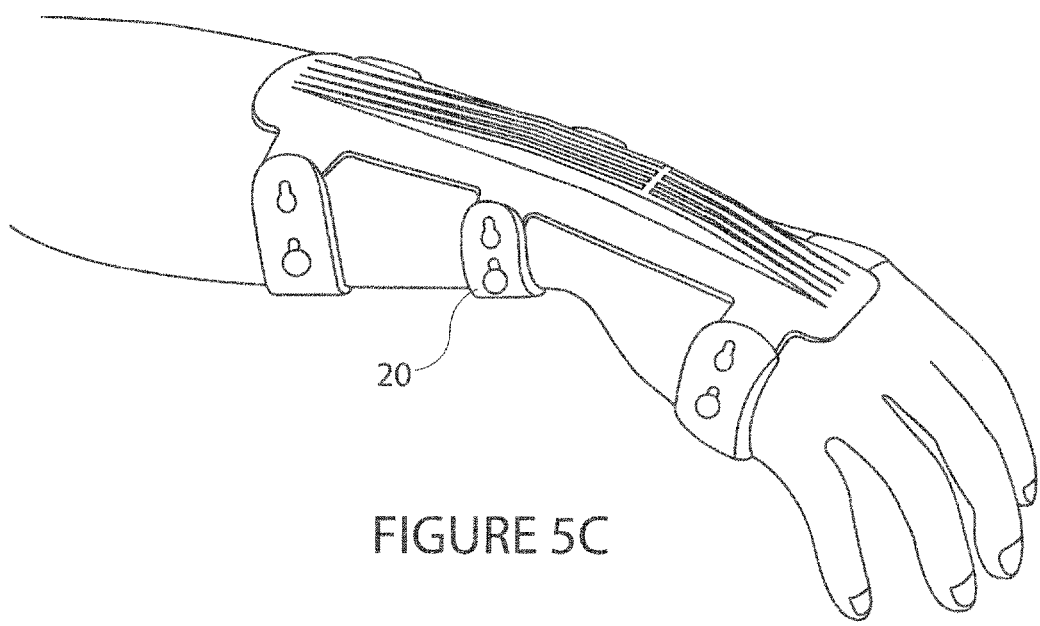

FIGS. 5A-5C show a fifth exemplary embodiment of a physical training device 10. According to this embodiment, brace portion 12 and fastening mechanism 14 are formed together from a single piece of material. Selection of a material may be in accordance with that described above for other embodiments. In a preferred embodiment, brace portion 12 and fastening mechanism 14 comprise molded rubber. Brace portion 12 may further comprise one or more ribs 13 molded into the material. Ribs 13 may provide added strength and/or structure to the brace portion 12 and to the overall device 10. Fastening mechanism 14 may comprise any combination of one or more straps, sleeve, cuff or glove as described above for other embodiments. As is shown in FIG. 5A, fastening mechanism 14 may comprise three molded straps 20. The straps may be secured to the user's arm, wrist, hand and/or fingers via any of the mechanisms described above. As shown in FIGS. 5B and 5C, one or more keyhole closures 40 may be used. Keyhole closure 40 comprises one or more molded ball studs 42 that may be securely inserted into one or more keyholes 44. The keyhole shape provides for a secure fit and also facilitates insertion and removal of the stud into and out of the keyhole. The studs may vary in width to facilitate a more secure fit in the keyhole. For example, the studs may comprise a ball or spherical shape. Multiple studs and/or keyholes may be used such that the fit of the device is adjustable and/or customizable to an individual user's preferences.

FIG. 6 shows a sixth exemplary embodiment of a physical training device 10, comprising a sleeve 18 having a sewn in brace 12. The sleeve may be shaped to match the contours of a user's arm, wrist, hand and/or fingers, thereby providing a more comfortable and/or secure fit for the user. Such a shape may also decrease the likelihood that the device may interfere with or detract from any activities that the user may participate in while using the device. The sleeve may comprise any of the materials described above. In one preferred embodiment, sleeve 18 comprises a nylon mesh material. A cutout or hole 50 may be formed into sleeve 18 to accommodate a user's thumb. In addition to providing a more comfortable and/or secure fit for the user, the cutout or hole may also serve to keep device 10 in position and to prevent the device from rotating or otherwise moving during use. Any of the closure mechanisms described above may be used to secure the device to the user's arm, wrist, hand and/or fingers. In a preferred embodiment, a single length of Velcro fasteners 22 may be provided along the bottom of sleeve 18 to secure the device to a user's arm, wrist, hand and/or fingers.

Figure 7A:
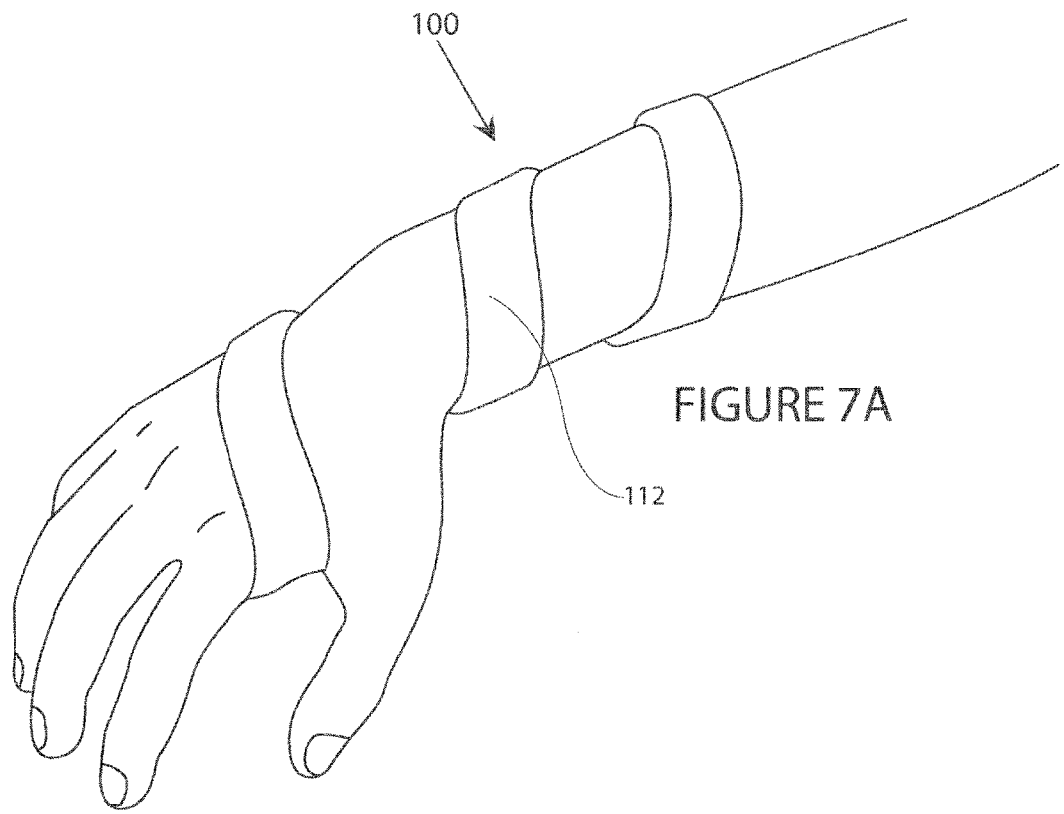
FIGS. 7a and 7b show a seventh exemplary embodiment of a physical training device in accordance with the present disclosure.
Figure 7B:
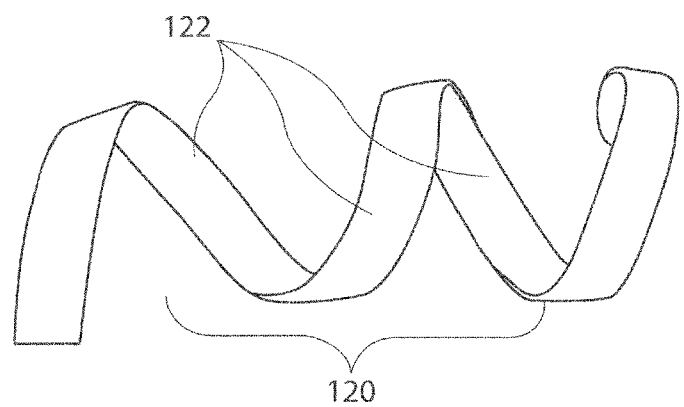

FIGS. 7A and 7B shows a seventh exemplary embodiment of a physical training device 100 in accordance with the present disclosure. In this embodiment, device 100 comprises brace portion 112. Brace portion 112 may comprise any materials known in the art, including aluminum, titanium, steel and alloys thereof. The metal may be plated, e.g., with chrome. Similarly, rubbers, molded rubbers, polymers and plastics known in the art may also be used. The brace portion 112 may further comprise various combinations of any two or more of the materials noted above or other materials known in the art. In a preferred embodiment, the brace portion 112 comprises aluminum. Brace portion 112 may further comprise padding along all or part of its length.

According to this embodiment, brace portion 112 may comprise a single length of aluminum or other material. The material should exhibit some degree of flexibility such that it can be shaped and molded to a user's preference. However, the material should also be rigid enough to hold a desired shape during use. A user may secure brace portion 112 to his or her arm, wrist, hand and/or fingers by wrapping brace portion 112 around portions of his or her arm, wrist, hand and/or fingers in a helical or spiral manner, as depicted in FIG. 7. The device may then be removed by unwrapping brace portion 112. Alternatively, brace portion 112 may be pre-shaped in a helical or spiral configuration. Accordingly, the user may secure the device by sliding the pre-shaped brace portion 112 onto his or her arm, wrist, hands and/or fingers. The user may then obtain a more secure fit by compressing the brace portion 112 against the user's arm, wrist, hand and/or fingers.

As shown in FIG. 7B, brace portion 112 may comprise a spiral or helix 120 with one or more loops 122. In a preferred embodiment brace portion 112 includes three separate loops 122, such that a first loop wraps around a user's hand, a second loop wraps around a user's wrist, and a third loop wraps around a user's arm when the device is in use. The number of loops, as well as their respective positions on the user, may be varied as needed to provide a more secure and/or comfortable fit, as well as to better retain the user's arm, wrist, hand and/or fingers in a desired position or conformation.

Figure 8A:
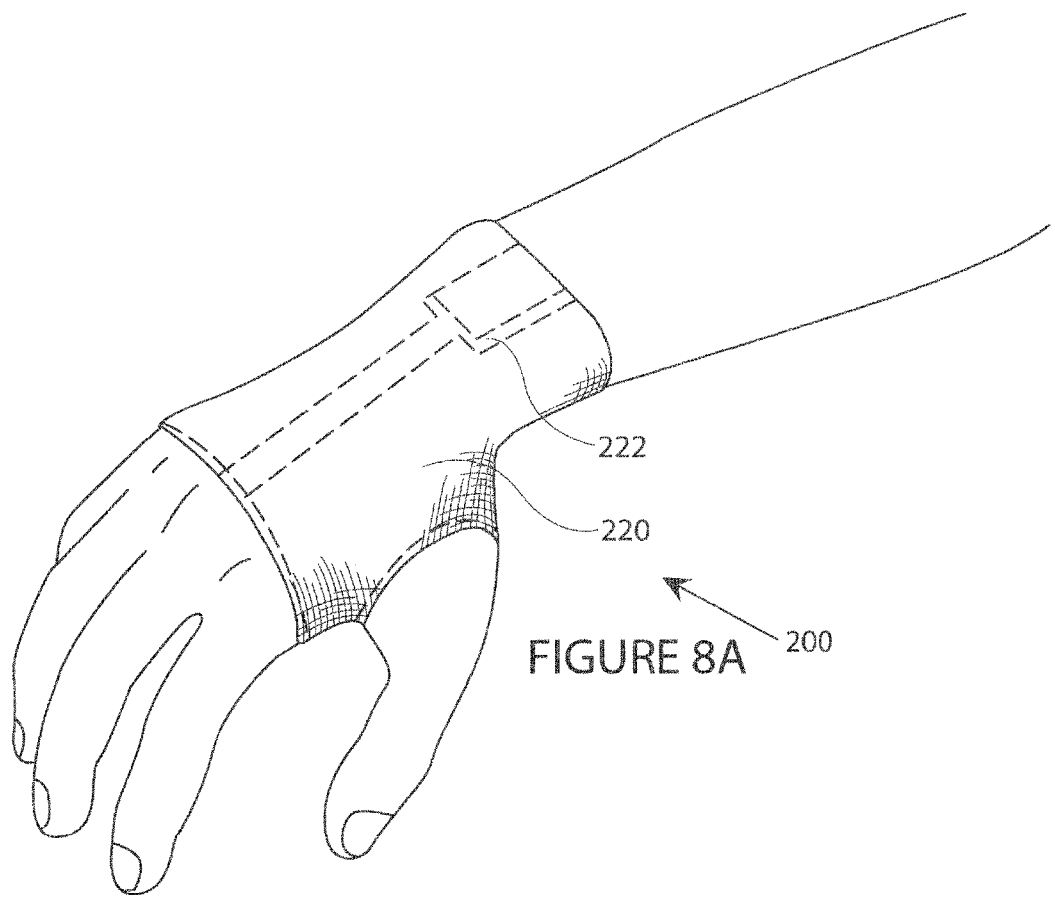
FIGS. 8a and 8b, and FIG. 9 shows an eighth exemplary embodiment of a physical training device in accordance with the present disclosure.
Figure 8B:
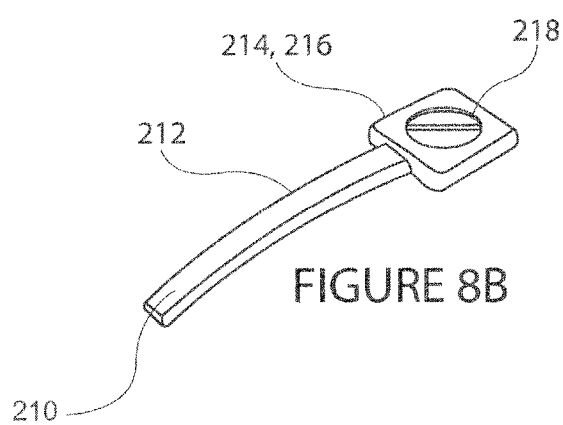
Figure 9:
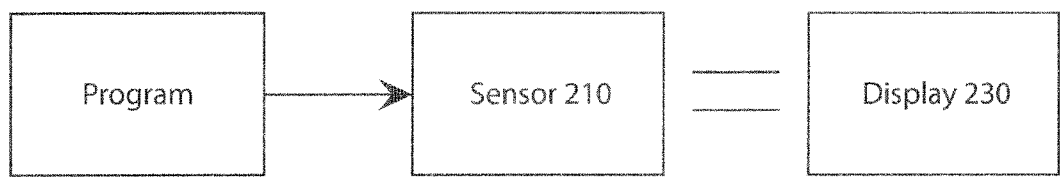

FIGS. 8A and 8B and 9 show an eighth exemplary and preferred embodiment of a physical training device according to the present disclosure. In this embodiment, device 200 includes a sensor 210 for detecting movement of a user's arm, wrist, hand and/or fingers. Sensor 210 may comprise a flex sensor such that the resistance of the sensor increases as the sensor is flexed or bent. Such a sensor may thereby detect flexing or bending of an object, material, or body part to which it is adjacent to or in contact. For example, a 4.5" flex sensor (Spectra Symbol SEN-08606) may be used. Other types of force and/or motion sensor known in the art may also be used.

Preferably sensor 210 is water-proof or resistant and/or sweat-proof or resistant. This may be achieved by covering or encasing the sensor in a material that is water-proof or resistant and/or sweat-proof or resistant or treated to be water-proof or resistant and/or sweat-proof or resistant. Any such material known in the art may be used including rubbers, polymers and plastics. In a preferred embodiment, a rubber overmold 212 at least partially covers sensor 210.

Sensor 210 may be in electrical communication with a printed circuit (PC) board 214 and feedback device 216. A power source 218 may also be in electrical communication with the PC board and output device. In a preferred embodiment, feedback device 216 comprises a speaker that provides audible feedback. Alternatively, feedback device 216 may be a device that provides visual or tactile feedback, such as an LED light, vibration mechanism, or other device known in the art. In the case of audible feedback, the device may optionally wirelessly send an audible signal to a separate speaker or headset. In a preferred embodiment, power source 218 may comprise a battery such as a button cell, watch cell, lithium cell, coin cell, or other battery known in the art.

Sensor 210 may be used in combination with a physical training device as described in any of the foregoing embodiments. In use, sensor 210 will be positioned at a location on the user's arm, wrist, hand and/or fingers which the user desires to monitor for movement. The movement may include rotational movement, angular movement, linear movement, or combinations of the foregoing. For example, sensor 210 may be positioned adjacent to or in contact with the user's wrist to detect bending, rotation or other movement of the wrist. The sensor 210 will detect if the monitored body part moves out of a desired position. When the monitored body part moves out of the desired position, sensor 210 will trigger feedback device 216 to provide audible, visual and/or tactile feedback to the user. The user thus becomes aware that the monitored body part has moved out of position and may then move the body part back into the desired position. The feedback may be provided in a single instance, intermittently or continuously until the user corrects the position of the body part. The sensitivity of sensor 210 may be adjusted such that it allows a small or large degree of movement from the desired position before it triggers the feedback device.

In a preferred embodiment, as shown in FIG. 8A, sensor 210 may be combined with a glove 220. Glove 220 may comprise any suitable material that is comfortable when worn against a user's skin, including many cloths, fabrics and similar materials known in the art. The material will also preferably be water-proof or resistant and/or sweat-proof or resistant, as well as soft and/or flexible. In a preferred embodiment, the material may comprise an elastic nylon mesh. Alternatively, a sewn nylon or molded rubber material may be used. As an alternative or in addition to a glove, a cuff, sleeve, partial sleeve, one or more straps, or a combination thereof may also optionally be used.

Glove 220 may comprise a stitched pocket 222 for securely holding sensor 210 and/or PC board 214, feedback device 216, and power source 218. Pocket 222 may be permanently shut or may be opened such that the components inside may be accessed, removed and/or replaced, if needed or desired. Alternatively, sensor 210 and related components may be attached, bonded, sewn or adhered to glove 220 via any method known in the art.

Referring also the FIG. 9, sensor 210 may be programmed to give sensory feedback to the wearer. Programming may be ecstatic programming or variable. Also, sensor 210 may include a wireless communications link for unloading information or feedback to a display 230 for user or coach or therapist (in the case of rehabilitation or physical therapy) feedback.

Figure 10:
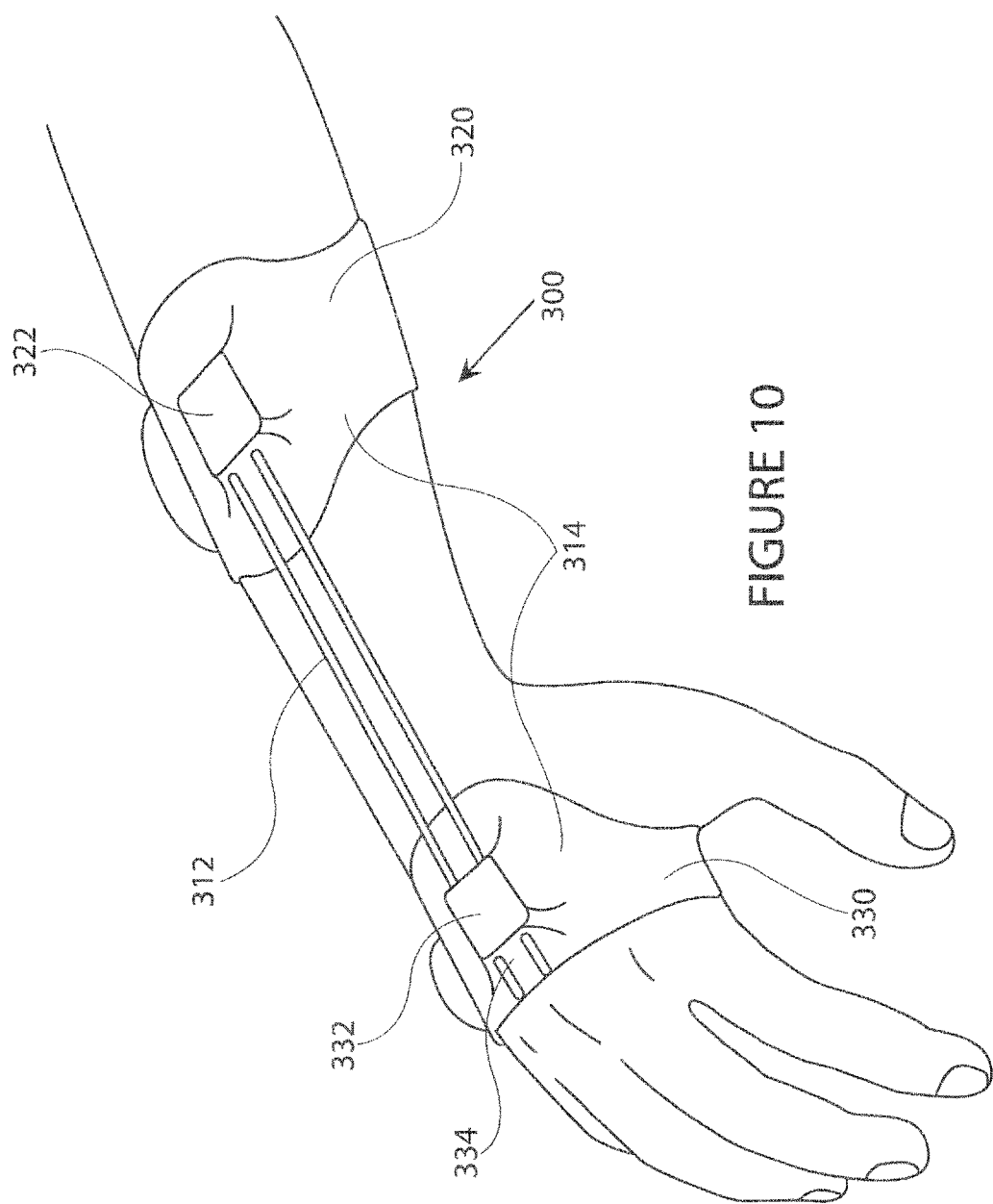
FIG. 10 shows a ninth exemplary embodiment of a physical training device in accordance with the present disclosure.

FIG. 10 shows a ninth exemplary embodiment of a physical training device according to the present disclosure. According to this embodiment, device 300 is adjustable in length to provide a more secure and/or comfortable fit for users of different sizes, ages, etc. Device 300 comprises a brace portion 312 and a fastening mechanism 314. Brace portion 312 may be as described above with respect to other embodiments, and thereby prevents or limits certain movements of the user's arm, wrist, hand and/or fingers when the device is in use. In a preferred embodiment, brace portion 312 may comprise two chrome plated steel rods. Fastening mechanism 314 secures the device adjacent to and/or in contact with a user's arm, wrist, hand and/or fingers. In a preferred embodiment, fastening mechanism 314 comprises two separate components: a first fastener 320 and a second fastener 330. Each of these components may comprise one of more of a strap, cuff, glove, sleeve or partial sleeve. In a preferred embodiment, the first fastener 320 comprises a cuff that may secure device 300 to a user's arm, and the second fastener 330 comprises a strap that may secure device 300 to a user's hand. These components may comprise material as described above with respect to those used in the fastening mechanisms of the other described embodiments. In a preferred embodiment, both components comprise molded silicone rubber. First fastener 320 and second fastener 330 may further be secured to a user's arm, wrist, hand and/or fingers via any of the closure mechanisms described above with respect to other embodiments, including Velcro, keyhole closure, snap, button, zipper, hook and eyelet closure, magnet, elasticized straps or bands, or combinations of any of the foregoing. In a preferred embodiment, both components may be secured via a keyhole closure.

First fastener 320 comprises a first receiving portion 322 for receiving an end of brace portion 312. Brace portion 312 may be securely attached to first receiving portion 322 such that it cannot move or be detached without significant effort. In a preferred embodiment, first receiving portion 322 comprises a protrusion extending out of first fastener 320. Brace portion 312 is securely anchored in the first receiving portion 322, as is shown in FIG. 9. First receiving portion 322 may be formed from the same material as the first fastener 320, or alternatively may comprise a separate part that is attached to the first fastener 320, e.g., via an adhesive or sewn to anchor component. In a preferred embodiment, first receiving portion 322 comprises molded silicone rubber formed from first fastener 320. Alternatively, first receiving portion 322 may be a pocket or depression formed in first fastener 320, or other structure capable of securely retaining brace portion 312.

Second fastener 330 comprises second receiving portion 332 for receiving brace portion 312. Second receiving portion 332 may be similar in structure and materials to first receiving portion 322. In a preferred embodiment, second receiving portion 332 comprises molded silicone rubber formed from the molded silicone rubber of second fastener 320. However, instead of securely retaining brace portion 312 as is the case with first receiving portion 322, second receiving portion 332 may receive brace portion 312 such that second receiving portion 332 may move along the length of brace portion 312. Accordingly, second receiving portion 332 comprises at least one hole or slot 334 through which brace portion 312 may pass. Hole or slot 334 may preferably be sized such that second receiving portion 332 can be moved along the length of brace portion 312 with minimal effort, but also able to retain second receiving portion 332 at a given position along brace portion 312 when no or little force is applied. In a preferred embodiment, second receiving portion 332 comprises two holes 334 for receiving brace portion 312, as depicted in FIG. 9. In various embodiments the relative positions of first and second fasteners along a user's arm may be varied, as well as the relative positions of the first and second receiving portions. In additional embodiments, the positions of both the first and second receiving portions may be adjustable or moveable along the brace portion.

Figure 11:
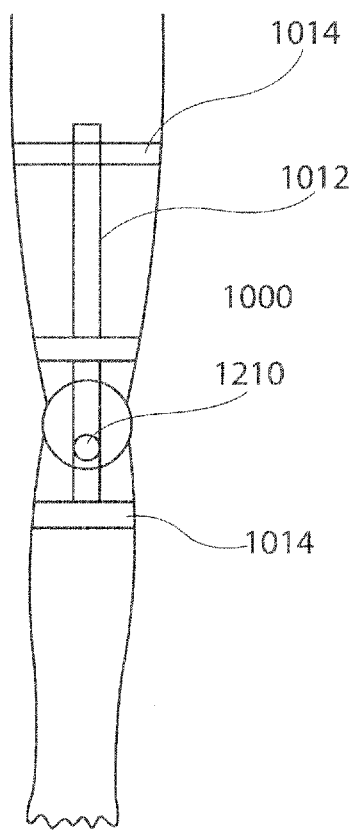
FIGS. 11, 12, 13 and 14 show tenth, eleventh, twelfth and thirteenth embodiments of physical training devices in accordance with the present disclosure.

FIG. 11 shows a physical training device according to a tenth exemplary embodiment of the present disclosure. The FIG. 11 embodiment 1000 includes a brace portion 1012 and a fastening mechanism 1014 securing the device adjacent to/or in contact with the user's thigh and knee. As before, the brace 1012 may be formed of a number of different materials, made varying size and length. The fastening mechanism may comprise straps, hook or loop fasteners, etc. as described above. Alternatively, the brace 1012 may be tubular in design fit snugly or tightly but comfortably against the user's thigh. Alternatively, the brace portion 1012 may be located on the wearer's lower leg. Preferably, a sensor 1210 is combined within the device 1000. Sensor 1210 is similar to sensor 1210 described above may be attached, bonded, sewn or adhered to brace 1012 or held in a pocket. Sensor 1210 may include PC board, feedback device, power source, etc, as before and should be positioned to measure the movement of the thigh or lower leg relative to the knee.

Figure 12:
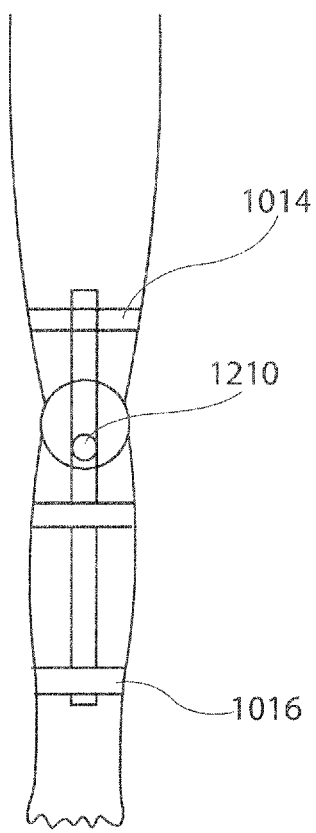

Yet another embodiment is shown in FIG. 12 which of the sensor 1210 is held in position relative to the ankle or foot for measuring movement thereof.

Figure 13:
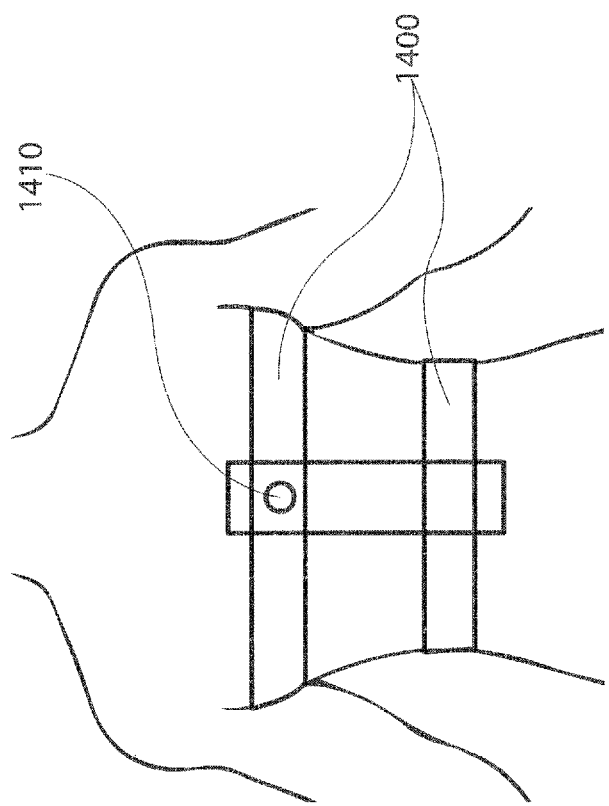

Referring to FIG. 13, in yet another embodiment, a physical training device in accordance with the present invention is held in contact with a wearer's back, for example a wrap which may be an elastic wrap 1400, or the sensor 1410 or fixed to a wearer's back by adhesive pads, tape or the like.

Figure 14:
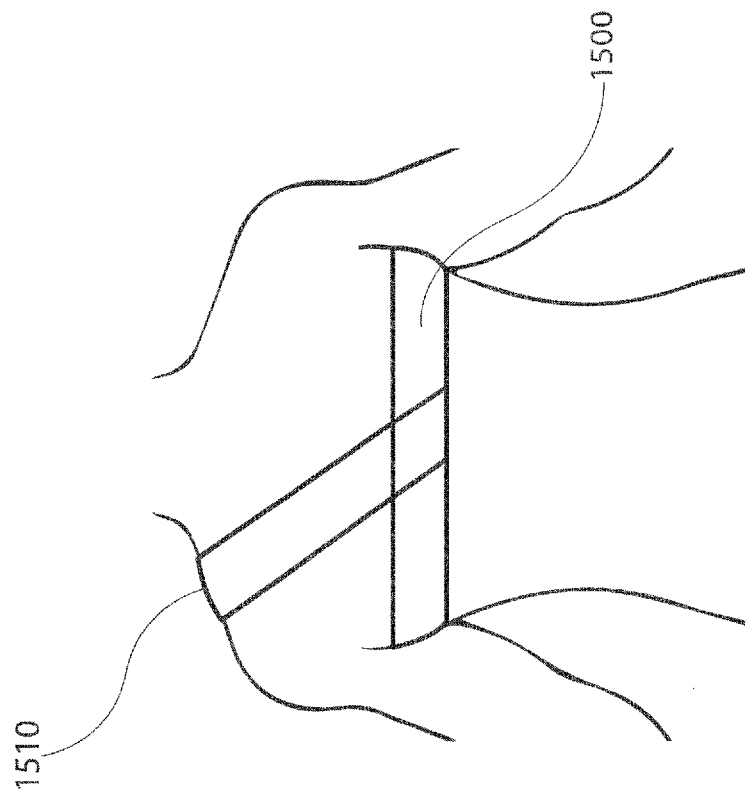

In still yet another embodiment shown in FIG. 14, the training device wrapped around the user's back (1500), and the sensor 151 is fixed to a wearer's shoulder and back or shoulder and arm, or neck and head, to provide training, feedback, etc, for motion of the back, shoulder or arm or neck and head.

It should be emphasized that the above-described embodiments of the present disclosure, particularly, any "preferred" embodiments, are merely possible examples of implementations, merely set forth for a clear understanding of the principles of the disclosure. Many other variations and modifications may be made to the above-described embodiments of the disclosure without departing substantially from the spirit and principles of the disclosure. All such modifications and variations are intended to be included herein within the scope of the present disclosure and protected by the following claims.

What is claimed is:

1. A sports training device comprising:
   a brace portion;
   a fastening mechanism adapted for securing the brace portion adjacent to a user's limbs, digits, joints, shoulders, legs, knees, ankles, feet, back, neck, head or hips, wherein the brace portion limits movement of a user's limbs, digits, joints, shoulders, legs, knees, ankles, feet, back, neck, head or hips when secured adjacent to or in contact with said user's limbs, digits, joints, shoulders, legs, knees, ankles, feet, back, neck, head or hips;

a sensor adapted for detecting a position or movement of the user's limbs, digits, joints, shoulders, back, neck, head or hips;

a feedback mechanism in communication with the sensor for providing audible, visual or tactical feedback to the wearer to correct the position or movement of the user's limbs, digits, joints, shoulders, back, neck, head or hips to a proper position or movement; and a wireless communication link for uploading position and/or movement information or feedback to a display;

wherein the sensor, the feedback mechanism and the wireless communication link are protected within a water-proof or resistant or sweat-proof or resistant enclosure.

2. The sports training device of claim 1, wherein the fastening mechanism comprises one or more fasteners selected from the group consisting of one or more straps, a sleeve, a cuff, a glove, hook and loop adhesive and combinations thereof.

3. The sports training device of claim 2, wherein the brace portion is enclosed or partially enclosed in a sleeve, cuff, glove or boot.

4. The sports training device of claim 3, wherein the sleeve, cuff or glove comprises a cutout to accommodate a user's thumb.

5. The sports training device of claim 2, wherein the fastening mechanism comprises nylon, vinyl, or rubber.

6. The sports training device of claim 1, wherein the length of the sports training device is adjustable.

7. The sports training device of claim 6, wherein the fastening mechanism comprises a first fastener, said first fastener comprising a first receiving portion for receiving the brace portion; and a second fastener, said second fastener comprising a second receiving portion for receiving the brace portion.

8. The sports training device of claim 7, wherein the first receiving portion receives the brace portion at a first position along a length of the brace portion and the second receiving portion receives the brace portion at a second position along a length of the brace portion, and wherein the position of one or both of the receiving portions along the length of the brace portion is moveable.

9. The sports training device of claim 1, wherein the brace portion is formed of a metal or rubber.

10. The sports training device of claim 9, wherein the brace portion is formed of aluminum or steel.

11. The sports training device of claim 1, wherein the sports training device is sized such that its length extends from the user's hand to the user's forearm or from the user's thigh or lower leg to the user's knee.

12. The sports training device of claim 1, wherein the sports training device further comprises padding.

13. The sports training device of claim 1, wherein the one or more fastening mechanisms are secured via at least one of the following: hook and loop, keyhole closure, snap, button, zipper, hook and eyelet closure, magnets, elastic and adhesive.

14. The sports training device of claim 1, wherein the brace portion further comprises ribs.

15. The sports training device of claim 1, wherein the brace portion comprises one or more rigid rods.

* * * * *